United States Patent [19]

Birchall et al.

[11] 4,064,266
[45] Dec. 20, 1977

[54] COMPOSITIONS FOR KILLING INTERNAL PARASITES CONTAINING 3-TERT-ALKYL-4-HYDROXY-5-HALO-BENZYLIDENE-MALONITRILES

[75] Inventors: George Richard Birchall, Kew; Donald William Gerald Harney, Doncaster; Bruce Adam Forsyth, Croydon, all of Australia

[73] Assignee: ICI Australia Limited, Melbourne, Australia

[21] Appl. No.: 720,660

[22] Filed: Sept. 7, 1976

[30] Foreign Application Priority Data

Sept. 29, 1975 Australia .............................. 3378/75

[51] Int. Cl.$^2$ .................. A61K 31/275; C07C 121/75
[52] U.S. Cl. ................................ 424/304; 260/465 E; 260/465 F
[58] Field of Search .................. 260/465 F, 465 E; 424/304

[56] References Cited

U.S. PATENT DOCUMENTS

| 3,149,148 | 9/1964 | Kladko et al. | 260/465 |
| 3,527,785 | 9/1970 | Ozaki et al. | 260/465 |

*Primary Examiner*—Dolph H. Torrence
*Attorney, Agent, or Firm*—Cushman, Darby & Cushman

[57] ABSTRACT

A compound of the general formula I

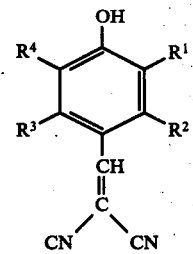

wherein $R^1$ is halogen, $R^4$ is a highly branched alkyl group, $R^2$ and $R^3$ which may be the same or different are hydrogen or halogen atoms or lower alkyl groups.

16 Claims, No Drawings

COMPOSITIONS FOR KILLING INTERNAL PARASITES CONTAINING 3-TERT-ALKYL-4-HYDROXY-5-HALO-BENZYLIDENE-MALONITRILES

This invention relates to compositions for killing internal parasites of warm blooded animals; in particular it relates to compositions for killing trematodes or nematodes. An example of a trematode is the liver fluke (*Fasciola hepatica*) which is a parasite of bile ducts of the liver of ruminants, such as cattle, sheep and goats. The liver fluke each year causes a significant amount of economic loss, not only from the death of the host animal but also from the deterioration in the value of meat and wool produced by infected animals. In cattle a loss in milk yield from liver fluke infection will also occur and in addition the loss sustained by the condemnation of infected livers as human food may also be considerable. An example of a nematode is Haemonchus contortus which is a nematode parasitic in the abnomasum or fourth stomach of ruminants. It is a blood sucking parasite and when present in large numbers can cause anaemia and finally the death of the host. It can cause extensive losses, not only in the value of the animals which it may kill but also in the diminished production of commercial items such as wool and meat. There is therefore a commercial need to treat animals with chemicals which are both safe and effective in reducing the incidence and severity of diseases caused by both trematodes and nematodes.

We have now found a new class of compounds which are effective in killing liver fluke.

Accordingly we provide a compound of the general formula I

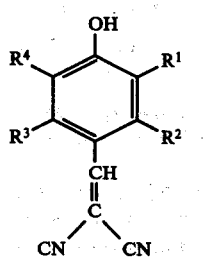

wherein $R^1$ is halogen, $R^4$ is a highly branched alkyl group, $R^2$ and $R^3$ which may be the same or different are hydrogen or halogen atoms or lower alkyl groups.

By lower we mean a group containing from 1 to six carbon atoms.

By highly branched alkyl group we mean a group wherein the carbon atom directly attached to the aromatic ring is substituted with three alkyl groups. Preferably $R^4$ is tert butyl or tert amyl.

Preferably $R^3$ is hydrogen and $R^2$ is hydrogen, halogen or methyl. We prefer that the phenols are not present as the free phenol but are in the derivative form, conveniently as a salt of a non-toxic base such as for example an alkali metal hydroxide or alkaline earth metal hydroxide, e.g., sodium hydroxide, amines such as, N-methyl-D-glucamine, diethanolamine, triethanolamine, N-methylglutamine or ammonia. The purpose of the salt is merely to increase the solubility of the active ingredient in aqueous formulations.

The compounds of our invention may be made by reacting an aldehyde of general formula II with malononitrile in the presence of a basic catalyst as shown below.

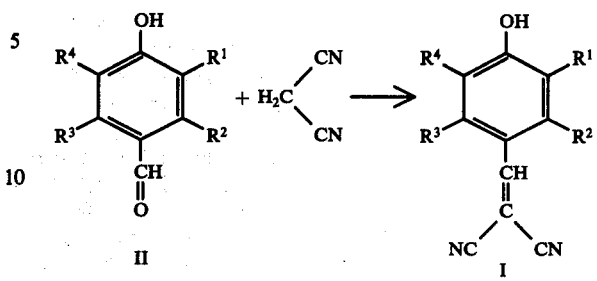

wherein $R^1$, $R^2$, $R^3$ and $R^4$ are as defined hereinbefore.

We also provide a method of treating warm blooded animals to eradicate certain internal parasites; which method comprises administering to said warm blooded animals a therapeutic dose of a composition comprising as active ingredient a compound as listed hereinbefore.

The compositions are of particular use for the treatment of *Fasciola sp* such as for example *Fasciola hepatica* and *Fasciola gigantica*.

For effective treatment, certain dosage levels are desired depending upon the compound employed, the type of animal to be treated, and the particular helminth being combatted. In general, effective fluke efficacy is achieved when the composition is administered in a single dose at dosage levels of from about 1 to 50 mg active ingredient/kg of animal body weight, and preferably from about 3 to 20 mg active ingredient per kg of animal body weight.

The compositions of the present invention may be administered in a variety of ways, depending upon the particular animal employed, the type of anthelmintic treatment normally given to such an animal, the materials employed, and the particular helminths being combatted. It is preferred to administer them in a single efficacious oral or parenteral dose at a time when fluke or nematode infection is apparent or suspected. They may be employed alone or in combination with other anthelmintics, parasiticides or antibacterials. The compounds may also be applied as a "pour on" formulation for dermal application. The amounts of the active anthelmintic ingredient in the composition, as well as the remaining constituents are varied according to the type of treatment to be employed, the host animal, and the particular parasitic disease being treated. In general, however, compositions containing a total weight percent of the active compound or compounds ranging from 0.001 to 95% will be suitable with the remainder being any suitable carrier or vehicle. Furthermore, the compositions should contain enough of the active ingredient to provide an effective dosage for the proper treatment of the parasitic disease.

A number of modes of treatment may be employed, and each to some extent determines the general nature of the composition. For example, the anthelmintic compositions may be administered to domesticated animals in single unit oral dosage form such as a tablet, bolus, capsule or drench; in a liquid form suitable for parenteral administration; or they may be compounded as feed premix to be later admixed with the animal's food.

When the compositions are to be solid unit dosage forms as in tablets, capsules, or boluses, the ingredients other than the active ingredient may be any other pharmaceuitcally acceptable vehicles convenient in the preparation of such forms, and preferably materials nutritionally suitable such as starch, lactose, talc, mangnesium stearate, vegetable gums, and the like. Moreover when capsules are employed, the active compound may be used in essentially undiluted form, the only extraneous material being that of the capsule casing itself which may be hard or soft gelatin or any other pharmaceutically acceptable encapsulating material. When the dosage form is to be used for parenteral administration, the active material is suitably admixed with an acceptable base vehicle. In all of such forms, i.e. in tablets, boluses, capsules, and injectable formulations, the active compound conveniently ranges from about 5 to 80% by weight of the total composition.

When the unit dosage form is to be in the form of a drench, the active ingredient may be mixed with agents which will aid in the subsequent suspending of the active compound in water, such as bentonite, clays, water-soluble starch, cellulose derivatives, gums, surface active agents and the like to form a dry predrench composition, and this predrench composition added to water just before use. In the predrench formulation, in addition to the suspending agent, such ingredients as preservatives, antifoam compounds, and the like may be employed. Such a dry product may contain as much as 95% by weight of the active compound, the rest being contributed by the excepients. Preferably, the solid composition contains from 30% to 95% by weight of the active compound. Enough water should be added to the solid product to provide the proper dosage level within a convenient amount of liquid for a single oral dose. Liquid drench formulations containing from about 10 to 50 weight percent of dry ingredients will in general be suitable with the preferred range being from 15 to 30 weight percent. Where the compositions are intended to be used as feeds, feed supplements, or feed premixes, they will be mixed with suitable ingredients of an animal's nutrient ration. The solid orally-ingestible carriers normally used for such purposes, such as distillers' dried grains, corn meal, citrus meal, fermentation residues, ground oyster shells, Attapulgus clay, wheat shorts, molasses solubles, corn cob meal, edible vegetable substances, toasted dehulled soya flour, soybean mill feed, antibiotic mycelia, soya grits, crushed limestone and the like are all suitable. The active compounds are intimately dispersed or admixed throughout the solid inert carrier by methods such as grinding, stirring, milling or tumbling. By selecting proper diluents and by altering the ratio of carrier to active ingredient, compositions of any desired concentration may be prepared. Feed supplement formulations containing from about 10 to 30% by weight of active ingredient are particularly suitable for addition of feeds. The active compound is normally dispersed or mixed uniformly in the diluent but in some instances may be adsorbed on the carrier.

These supplements are added to the finished animal feed in an amount adequate to give the final concentration of active ingredient desired for controlling or treating the helminth infection by way of the animal ration. Although the preferred level in feeds will depend on the particular compounds being employed, the active ingredients of this invention are normally fed at levels of 0.05 – 25% in the feed. As stated above, animals are preferably treated at a time when the infestation is apparent or suspected.

Thus administration of medicated feed is not preferred but may certainly be employed. Similarly, the amounts of drugs present in the feed may be reduced to levels in the order of 0.001% to 3.0 weight percent based on the weight of feed, and the medicated feed administered over prolonged periods. This would be in the nature of a preventive or propylactic measure but again is not the mode of choice. Another method of administering the compositions of this invention to animals whose feeds are conveniently pelleted, such as sheep, is to incorporate them directly in the pellets. For instance, the compositions are readily incorporated in nutritionally adequate alfalfa pellets at levels of 2 to 110 grams per pound of pellets for therapeutic use, and at lower levels for example 80 to 1000 milligrams per pound for prophylactic use, and such pellets fed to the animals. The compositions may also optionally contain other drugs of veterinary utility. Veterinary drugs which may be present in the veterinary compositions of this invention, depending upon the mode of administration of the said compositions, include for example, piperazine, 1-diethyl-carbamyl-4-methyl-piperazine, tetrachloroethylene, organic and inorganic arsenical compounds, tetramisole, 2-phenyl-benzimidazole, thiabendazole, phenothiazine, mebendazole and pyrantel salts.

The compositions may be administered to the animal by parenteral dose and in a further aspect of our invention we provide an injectable composition comprising a sterile solution containing from 5 to 70% w/w preferably 5 to 50% w/w of the active ingredient in a pharmaceutically acceptable solvent.

The composition may be sterilized by methods known to those skilled in the art for the sterilization of injectable solution such as, for example, ultra filtration or gamma radiation.

The invention is now illustrated by, but by no means limited to, the following examples in which all parts are part by weight unless otherwise specified.

EXAMPLE 1

3-Bromo-5-tert-butyl-4-hydroxybenzylidenemalononitrile

3-Bromo-5-tert-butyl-4-hydroxybenzaldehyde (1.5 gm), malononitrile (0.6 gm), piperidine (six drops) and benzene (20 ml) were refluxed under a Dean and Stark water separator for 1.5 hr. The benzene was removed in vacuo and the residue crystallised from alcohol as pale yellow needles of 3-bromo-5-tert-butyl-4-hydroxybenzylidenemalononitrile (0.9 gm) m.p. 185°.

In a similar manner starting from the appropriate aldehyde 3-iodo-5-tert-butyl-4-hydroxybenzylidenemalononitrile formed pale yellow needles from ethylene dichloride m.p. 188° and 3-chloro-5-tert-butyl-4-hydroxybenzylidenemalononitrile formed pale yellow needles from ethanol m.p. 171°.

EXAMPLE 2

3-tert-butyl-4-hydroxy-5-iodobenzylidenemalononitrile 3-tert-butyl-4-hydroxy-5-iodobenzaldehyde (24.8 gm), malononitrile (6.2 gm), piperidine (1.0 ml), acetic acid (3.3 ml) and benzene (300 ml) were refluxed under a Dean and Stark water separator for 2 hours. On cooling a crystalline precipitate formed and was filtered off. Recrystallisation from ethylene dichloride gave pale yellow needles of 3-tert-butyl-4-hydroxy-5-iodobenzylidenemalononitrile (24.2 gm) m.p. 188°.

The starting aldehyde was prepared as follows:

Chloroform (95 gm) was added dropwise with mechanical stirring to a mixture of sodium hydroxide (120 gm), water (120 gm) methanol (50 ml) and o-tert-butylphenol (100 gm) over 2 hours at 50° C. The mixture was stirred at 50° for 1 hour and then poured into water (600 ml) and acidified to pH5 with concentrated hydrochloric acid. The oily layer that formed was collected and steam distilled. The residue from the steam distillation was taken into chloroform (200 ml) and extracted with 2N sodium hydroxide. The basic extracts were acidified and the product formed was crystallised from petroleum ether to give 3-tert-butyl-4-hydroxybenzaldehyde as colourless prisms m.p. 142°.

A slurry of 3-tert-butyl-4-hydroxybenzaldehyde (16 gm) sodium hydroxide (3.5 gm), potassium iodide (10.3 gm), potassium in distilled water (91 ml) was added dropwise during 20 mins to a stirred solution of ethanol (69 ml), water (15 ml) and and concentrated sulphuric acid (7.5 ml) at 50°–55° C. After addition, the mixture was refluxed for 1 hour. Sodium metabisulphite (1 gm) was added to the mixture and on cooling a precipitate formed. The precipitate was collected and recrystallised from petroleum ether to give 3-tert-butyl-4-hydroxy-5-iodobenzaldehyde (24.8 gm) m.p. 124°.

EXAMPLE 3

In a similar manner as described in Example 2 reaction of 3-bromo-5-tert-butyl-4-hydroxybenzaldehyde and malononitrile gave 3-bromo-5-tert-butyl-4-hydroxybenzylidenemalononitrile as pale yellow needles from alcohol m.p. 185°.

3-bromo-5-tert-butyl-4-hydroxybenzaldehyde was prepared as follows:

To 3-tert-butyl-4-hydroxybenzaldehyde (3 gm) in acetic acid (30 ml) was added dropwise bromine (1.5 ml). The mixture was stirred at 25° for 3 hours and the solvent removed in vacuo. Recrystallisation of the residue from aqueous ethanol gave 3-bromo-5-tert-butyl-4-hydroxybenzaldehyde (3.2 gm) m.p. 126°.

In a similar manner as described in Example 2 reaction of 3-tert-butyl-5-chloro-4-hydroxybenzaldehyde and malononitrile gave 3-tert-butyl-5-chloro-4-hydroxybenzylidenemalononitrile m.p. 173°.

3-tert-butyl-5-chloro-4-hydroxybenzaldehyde was prepared as follows:

Chlorine gas was passed into a solution of 3-tert-butyl-4-hydroxybenzaldehyde (2.5 gm) in acetic acid (20 ml) for 1 hour. The solution was poured into water and the product collected. Recrystallisation from aqueous ethanol gave 3-tert-butyl-5-chloro-4-hydroxybenzaldehyde m.p. 123° C.

EXAMPLE 4

In a similar manner as described in Example 2 reaction of 3-tert-butyl-4-hydroxy-5-iodo-6-methylbenzaldehyde and malononitrile gave 3-tert-butyl-4-hydroxy-5-iodo-6-methylbenzylidenemalononitrile as prisms from ethylenedichloride m.p. 158°.

3-tert-butyl-4-hydroxy-5-iodo-6-methylbenzaldehyde was prepared from 2-tert-butyl-5-methylphenol by formylation followed by halogenation as described in Example 2.

In a similar manner as described in Example 2 reaction of 3-bromo-5-tert-butyl-4-hydroxy-2-methyl-benzaldehyde and malononitrile gave 3-bromo-5-tert-butyl-4-hydroxy-2-methylbenzylidenemalononitrile m.p. 144°.

The starting aldehyde was prepared in a similar manner to that described above.

EXAMPLE 5

In a similar manner starting from the appropriate aldehyde 5-tert-butyl-2, 3-dichloro-4-hydroxybenzylidenemalononitrile m.p. 169°, 3-bromo-5-tert-butyl-2-chloro-4-hydroxybenzylidenemalononitrile m.p. 154°, 5-tert-butyl-2-chloro-4-hydroxy-3-iodobenzylidenemalononitrile m.p. 169°, 5-tert-butyl-2,3-dibromo-4-hydroxybenzylidenemalononitrile m.p. 167° was prepared.

The starting aldehydes were prepared in a similar manner to that described above.

EXAMPLE 6

Compositions suitable for use as experimental aqueous oral drenches were prepared in the following general manner. A mixture of the required amount of active ingredient was mixed with 40 ml of an aqueous 0.25% w/w solution of "Lubrol E" ("Lubrol E" is a Trade Mark for an octylphenol ethoxylate). The mixture was ball-milled for 30 minutes and the resultant suspension was used as an aqueous drench.

EXAMPLE 7

Compositions suitable for use as experimental injectable solutions were prepared by dissolving the chemical in an appropriate solvent and sterilising the solution by ultra-filtration and adjusting the concentration to 10% w/v active ingredient.

EXAMPLE 8

Compositions prepared by the methods of Examples 6 and 7 were used as a single dose to test sheep infected with sheep liver fluke (*Fasciola hepatica*). The number of liver fluke eggs in the faeces was measured at the time of treatment and 3, 7 and 14 days after treatment. The sheep were killed on day 14 and the number of adult flukes in the liver counted. The amount and structure of active ingredient in each composition and the results of treatment of a sheep with that composition are given in the Table I below.

TABLE I

| Active Ingredient | | Faecal Egg Count (Eggs) per g of faeces) on day | | | | Post Mortem Results |
|---|---|---|---|---|---|---|
| Structure | Dose Rate mg/Kg | 0 | 3 | 7 | 14 | No of Adult Fluke |
| OH, I, CH=C(CN)CN (tert-butyl) | 10 p.o. | 210 | 30 | 110 | 20 | 0 |
| | 5 p.o. | 690 | 700 | 110 | 20 | 0 |
| | s.c. | 700 | 480 | 380 | 10 | 0 |
| | 5 s.c. | 200 | 10 | 10 | 0 | 0 |
| | *5 s.c. | 220 | 30 | 0 | 20 | 0 |
| | *25 s.c. | 140 | 50 | 40 | 10 | 0 |
| | **5 s.c. | 410 | 120 | 0 | 0 | 0 |
| | **25 | | | | | |

TABLE I-continued
| Active Ingredient Structure | Dose Rate mg/Kg | Faecal Egg Count (Eggs per g of faeces) on day | | | | Post Mortem Results No of Adult Fluke |
|---|---|---|---|---|---|---|
| | | 0 | 3 | 7 | 14 | |
| 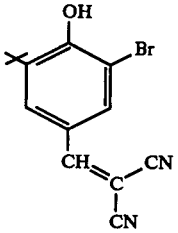 | 12.5 p.o. 5 p.o. | 150 420 | 40 50 | 0 10 | 10 0 | 0 1 |
| 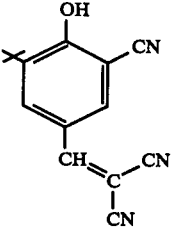 | 10 p.o. 5 p.o. | 1860 840 | 90 40 | 0 0 | 20 0 | 0 1 |
| 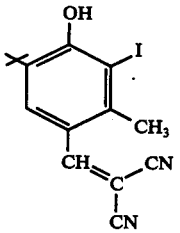 | 10 p.o. | 400 | 220 | 0 | 0 | 0 |
| 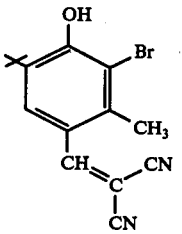 | 12.5 p.o. | 190 | 10 | 10 | 10 | 0 |
| 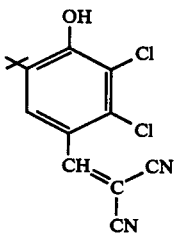 | 10 s.c. | 250 | 20 | 140 | 0 | 0 |
| 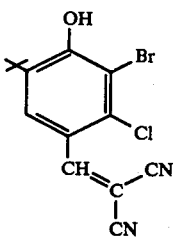 | 10 p.o. 10 s.c. | 1300 1060 | 30 220 | 0 0 | 20 0 | 5 0 |

TABLE I-continued

| Active Ingredient Structure | Dose Rate mg/Kg | Faecal Egg Count (Eggs per g of faeces) on day 0 | 3 | 7 | 14 | Post Mortem Results No of Adult Fluke |
|---|---|---|---|---|---|---|
| 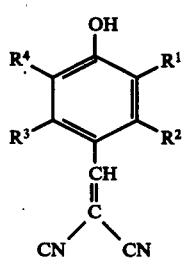 | 10 p.o | 500 | — | 1320 | 20 | 2 |

*3-tert-butyl-4-hydroxy-5-iodobenzylidenemalononitrile (64 gm) and N-methyl-D-glucamine (8 gm) were dissolved in distilled water (100 ml). The solution was sterilised by ultra-filtration.
**3-tert-butyl-4-hydroxy-5-iodobenzylidenemalononitrile (1 gm) and N-methyl-D-glucamine were dissolved in dimethylacetamide (10 ml). The solution was sterilised by ultra-filtration.

We claim:
1. A compound of the formula wherein $R^1$ is halogen, $R^4$ is an alkyl wherein the carbon atom directly attached to the aromatic ring is substituted with three alkyl groups, $R^2$ and $R^3$ which may be the same or different are hydrogen, halogen or lower alkyl, or a salt of such compound with non-toxic base.

2. A compound according to claim 1 wherein $R^4$ is tert butyl or tert amyl.

3. A compound according to claim 1 wherein $R^3$ is hydrogen and $R^2$ is hydrogen, halogen or methyl.

4. A compound according to claim 1 wherein $R^1$ is chlorine, bromine or iodine, $R^2$ is hydrogen, methyl, chlorine or bromine, $R^3$ is hydrogen.

5. The compound 3-tert-butyl-4-hydroxy-5-iodobenzylidenemalononitrile.

6. The compound 3-bromo-5-tert-butyl-4-hydroxybenzylidenemalononitrile.

7. The compound 3-tert-butyl-5-chloro-4-hydroxybenzylidenemalononitrile.

8. The compound 6-methyl-3-tert-butyl-4-hydroxy-5-iodobenzylidenemalononitrile.

9. The compound 2-methyl-3-bromo-5-tert-butyl-4-hydroxybenzylidenemalononitrile.

10. The compound 5-tert-butyl-2,3-dichloro-4-hydroxybenzylidenemalononitrile.

11. A compound according to claim 1 comprising the salt of a compound of general formula I with a base selected from the group consisting of N-methyl-D-glucamine, diethanolamine, sodium hydroxide, triethanolamine, 2-diethylaminoethanol.

12. A method of treating warm blooded animals to eradicate certain internal parasites, which method comprising administering to the said warm blooded animal a therapeutic dose of a composition comprising as active ingredient a compound according to claim 1.

13. A method according to claim 12 wherein the therapeutic dose is from 1 to 50 mg active ingredient per kg of animal body weight.

14. A method according to claim 13 wherein the therapeutic dose is from 3 to 20 mg/kg.

15. A sterile injectable composition for treatment of warm blooded animals comprising, as active ingredient, from 5 to 70% w/v of a compound according to claim 1 in a pharmaceutically acceptable solvent.

16. A sterile injectable composition according to claim 15 comprising from 5 to 50% w/v of active ingredient.

* * * * *